United States Patent [19]

Feldman et al.

[11] 4,065,580

[45] Dec. 27, 1977

[54] LIPOLYTIC ENZYME FLAVORING SYSTEM

[75] Inventors: Louis I. Feldman, Morton Grove; J. Gordon Dooley, Glenview, both of Ill.

[73] Assignee: GB Fermentation Industries, Inc., Kingstree, S.C.

[21] Appl. No.: 632,605

[22] Filed: Nov. 17, 1975

Related U.S. Application Data

[63] Continuation of Ser. No. 458,737, April 8, 1974, abandoned.

[51] Int. Cl.² .................. A23D 5/00; A23C 19/00; C07G 7/02
[52] U.S. Cl. ........................... 426/33; 426/35; 426/36; 426/38; 195/62; 195/66 R
[58] Field of Search ............ 426/33, 35, 36, 34, 426/38; 195/66, 62

[56] References Cited

U.S. PATENT DOCUMENTS

3,549,390 12/1970 Charles et al. .................. 426/36
3,616,233 10/1971 Schleich ........................ 195/66 R

FOREIGN PATENT DOCUMENTS

1,262,943 2/1972 United Kingdom.
1,207,892 10/1970 United Kingdom.

OTHER PUBLICATIONS

Nelson, J. H., Enzymatically Produced Flavors for Fatty Systems, J. of the American Oil Chemists Society, vol. 49, 1972, (pp. 559–562).

Harper, W. J., Lipase Systems Used in the Manufacture of Italian Cheese, J. Dai. Sci., vol. 40, 1957, (pp. 556–563).

*Primary Examiner*—David M. Naff
*Attorney, Agent, or Firm*—Hammond & Littell

[57] ABSTRACT

A lipolytic enzyme preparation having 1 part of lipase activity to from 1 to about 10 parts of esterase activity is obtained from *Mucor miehei*. The enzyme preparation can be recovered substantially free of *Mucor miehei* rennet, and is useful for treating various triglyceride fats to provide desirable flavors.

21 Claims, No Drawings

LIPOLYTIC ENZYME FLAVORING SYSTEM

This is a continuation, of application Ser. No. 458,737, filed Apr. 8, 1974, now abandoned.

This invention relates to an enzymatically produced flavoring system by certain species of the genus Mucor and, more particularly, to the production of an improved lipolyzed fat by an enzyme preparation obtained from *Mucor miehei*.

Enzymatically produced flavors are common to many types of foods, especially those which are produced by fermentation. For example, in the manufacture of food products such as bakery goods, coffee whiteners, milk chocolate, margarine and the like it is desirable to have a milk or butter-like flavor in the finished product. In certain types of cheeses and cheese products, especially the so-called soft cheeses and strong cheeses such as the Italian-type varieties, distinct flavor are dependent on various enzyme systems employed during the cheese production.

In the case of fat bearing foods, the principal enzymatic action is a lipolysis or an enzyme-catalyzed hydrolytic cleavage of triglycerides. Although other enzymatic flavor developments can occur concurrently with lipolysis, the present invention is concerned principally with the latter type of activity.

Of course, spontaneous or uncontrollable lipolysis has plagued the food industry for many years, since undesirable flavors, or harsh rancidity, can result thereby. In recent years, however, the development of controlled lipolysis has resulted in many improved food products. Thus, it is common practice in the dairy industry to treat milk fats will lipolytic enzymes to produce desired flavors. The lipolytic enzyme acts on the triglycerides to produce free fatty acids which, in turn, can be further converted to other compounds, such as ketones, in some instances. The amount and type of fatty acids produced are dependent on the amount and type of fat in the food product, the amount and type of lipolytic enzyme product and the time and temperature of treatment with lipolytic enzyme. Further background on conventional controlled lipolysis can be found in J. Amer. Oil Chem. Soc. 49, 559–62 (1971), and references cited therein.

In accordance with the present invention an improved flavoring system is provided for triglyceride fats and fat bearing foods and, in particular, an improved lipolyzed milk fat, by an enzyme preparation from *Mucor miehei*.

Various lipolytic enzymes are known, for example, pancreatic lipase, pregastric esterase, milk lipase and fungal lipase. In particular, the fungal lipases are obtained, for example, from Aspergillus as disclosed in U.S. Pat. No. 2,480,090, from Rhizopus as described in U.S. Pat. No. 3,262,863, and from Mucor as seen from U.S. Pat. No. 3,616,233. The effect of these fungal lipases for developing rancidity in fats with respect to Aspergillus is disclosed in J. Gen. Appl. Microbiol. 10, 13-22 (1964); with respect to Rhizopus is described in Agr. Biol. Chem. 33, 729-38 (1969); and with respect to Mucor is set forth in Appl. Microbiol 16, 617–19 (1968), and 17, 606-10 (1969). Typical commercially available esterases and lipases used heretofore are pregastric esterases such as those available from Dairyland Food Laboratory under the trade names Italase and Capalase; the pancreatic lipase available from Fermco Laboratories under the trade name Fermlipase PL; and the fungal lipase available from Rohm and Hass under the trade name Lipase B.

Due to the shortage of animal derived lipolytic enzymes, the obtention of lipolytic enzyme systems from a microbial source offers the potential advantage of greater availability and, furthermore, the likelihood of a product of more uniform quality through controlled fermentation of the organism. However, not all microbial lipolytic enzymes provide a desired flavoring system.

It has now been found that an excellent quality, enzymatically produced triglyceride fat flavoring system can be obtained from the microbial organism *Mucor miehei*. This enzymatic flavoring system is defined herein in terms of the ratio of esterase activity (EA) to lipase activity (LA) or EA/LA.

As defined herein, the esterase activity is that activity of the enzyme on the water-soluble fats, namely those fats having carbon chain lengths of from about 4 to about 10. Conversely, the lipase activity is that activity of the enzyme on the water-insoluble fats, namely those fats having carbon chain lengths of about 12 and higher, particularly 12 to 22.

In accordance with the present invention, it has been unexpectedly discovered that the lipolytic enzyme system produced by certain species of the genus Mucor, and particularly *Mucor miehei*, as opposed to that of other fungi, such as Aspergillus and Rhizopus, has the desirable property of expressing greater esterase activity than lipase activity, in a manner similar to that of commercially employed pregastric esterases from calf, kid and lamb. That is, it shows an EA/LA ratio of greater than one. By way of comparison, Aspergillus and Rhizopus produced lipolytic systems have been found to show EA/LA ratios of less than one, and consequently are unsuitable for the purposes of this invention. Preferably, the EA/LA ratio is greater than two and ratios of about 2 to 10 are eminently suitable in accordance with the present invention.

The esterase activity preferably is measured by a test on tributyrin whereas the lipase activity preferably is measured by a test on an olive oil substrate. These tests can be carried out as follows.

ESTERASE METHOD

This method is used to determine the esterase that hydrolyzes tributyrin. Esterase is incubated with a tributyrin solution at pH 6 and 37° C. The acid is liberated in the reaction mixture during 40 minutes is titrated to pH 8.7. The results reflect a practically linear relationship between reaction rate and enzyme concentration within recommended range.

Solutions

1. Substrate solution.

Add 13 grams gum arabic U.S.P. to 114 ml 0.05M sodium acetate solution (6.8 g $NaC_2H_3O_2 \cdot 3H_2O$ to 1 liter), then add about 50 mg thymol and stir 25 minutes to dissolve. Add 22.7 g tributyrin (75 m mole) to the buffered gum solution and emulsify in a Waring Blender for 5 minutes. Adjust the emulsion with 0.5N NaOH to pH 6.0. Less than 1 ml of the alkali is needed. The solution can be used for at least 3 days when stored in a refrigerator. Before each use shake well and re-adjust to pH 6.0 if necessary.

For the "enzyme blank" (see "Controls" below) use a solution of 13 g gum arabic in 114 ml 0.05M sodium acetate. Adjust the gum-acetate solution to pH 6.0, which requires 3 to 4 ml 0.1N NaOH.

2. 0.02N NaOH.

3. Acetate buffer, pH 5.9 to 6.2, 0.05M.

Dissolve 6.8 g sodium acetate .3H$_2$O in about 500 ml water, add 1.0 ml 1N HCl and make to 1 liter with distilled water.

4. Enzyme solutions.

Prepare all solutions and serial dilutions with acetate buffer (No. 3, above).

The required concentrations are described under "Range" below.

Procedure

Shake substrate solution and pipette 50.0 ml into a 125 ml Erlenmeyer flask. Add 10.0 ml of enzyme solution, mix quickly and remove a 10.0 ml aliquot which is added to 40 ml water and immediately titrated with 0.02N NaOH to pH 8.7. Immediately after the removal of the aliquot place the remaining mixture in a 37° bath (which is considered the zero time point) where it is kept for 40 minutes with continuous stirring (immersed magnetic stirrer). Exactly 40 minutes after the zero time point, remove another 10.0 ml aliquot, place into 40 ml water and titrate to pH 8.7. The difference between the two titrations expresses the degree to which the tributyrin has been hydrolyzed by the enzyme.

Controls

A substrate blank is not needed but crude enzyme preparations may require an enzyme blank. Proceed as described above but use the adjusted gum arabic solution without tributyrin instead of the regular substrate solution. Correct the main result by subtrating the titration increase found for the control.

Units

One unit of esterase produces under the conditions of the test one microequivalent acid per minute. Esterase activity (EA) is the number of units per gram of preparation.

Calculation $$EA = \frac{\text{ml NaOH} \times \text{N NaOH} \times 1000 \times \text{ml digested mixture}}{\text{minutes} \times \text{g preparation in digested mixture} \times \text{ml aliquot}} \quad (1)$$

where ml NaOH is the titration increase for a 10 ml aliquot and N NaOH is the normality of the NaOH used for the titration.

$$\text{Thus: } EA = \frac{\text{ml NaOH} \times 0.02 \times 1000 \times 60}{40 \times \text{g preparation} \times 10} \quad (2)$$

$$EA = \frac{\text{ml NaOH} \times 3}{\text{gram preparation in digested mixture}} \quad (3)$$

Range

Sample dilution should be such that titration increases between 0.5 and 1.5 ml are obtained. Repeat tests should be made, if necessary, to obtain results within this range.

The progress of the tributyrin hydrolysis is linear with time and it is possible to run the assay at shorter than 40 minute digestion periods. Naturally, equation (3) has then to be adjusted by the appropriate time factor.

Lipase Method

This method is used to determine the lipase that hydrolyzes olive oil. Lipase is incubated with an olive oil emulsion at pH 6.5 and 30° C. The acid that is liberated in the reaction mixture during 5 minutes is titrated to pH 8.0.

The results reflect a practically linear relationship between reaction rate and enzyme concentration within recommended range.

Chemicals

1. Olive oil, U.S.P.
2. Amerchol L-101 (lanolin-derived free sterols), American Cholesterol Products, Edison, New Jersey.
3. Sodium barbital, N.F.
4. Gum arabic, U.S.P.
5. Sodium acetate .3H$_2$O,C.P.
6. Sodium chloride, C.P.
7. 0.5N NaOH.
8. 0.02N NaOH.
9. 0.1N HCl.
10. Ethyl Alcohol (denatured No. 23A is suitable).

Equipment

1. Waring Blender.
2. Two magnetic stirrers, one of which is suitable for submersion in water bath (Model MS-7, Tri-R Instruments, Jamaica, New York).
3. pH meter for titrations, equipped with a small combination electrode (such as No. 4858-L15, A. H. Thomas).
4. Microburette, 10 ml. with 0.02 ml. divisions (Kimble No. 17107F with Luer type syringe neddle 20G, 1- inches).

Solutions

1. Substrate Emulsion.
  Stir 30 g gum arabic and 270 ml distilled water magnetically for 30 minutes at room temperature. Break any lumps present with a glass rod. Cool to 5° C. Weight 6 g Amerchol into a 400 ml beaker, add 72 g olive oil and 222 g of the chilled gum arabic solution. Stir with a glass rod and pour into Waring Blender. Blend 5 minutes. Adjust to pH 6.3 with 0.5 N NaOH, cool to 5° C and blend again for 7 minutes. The temperature may have increased to a maximum of 47° C and the pH to 6.5. If not, adjust to pH 6.5. The emulsion is stable for at least 8 days when stored in the refrigerator. The temperature should not be allowed to drop below 1° C.
2. Buffer.
  a. Stock solution. Dissolve 9.7 g sodium acetate. 3H$_2$O and 14.7 g sodium barbital with distilled water to 500 ml. This solution is 0.14 N barbital and 0.14 N acetate, pH 9.9. Store in refrigerator.
  b. Working solution. Dilute 40 ml stock solution, 16 ml 8.5% NaCl solution and 53 ml 0.1N HCl with distilled water to 200 ml., pH 6.5. For minor adjustments use 0.1N HCl or 0.1N NaOH. Store in refrigerator. Discard if crystals appear during storage.
3. Enzyme solutions.
  For the assay of solid preparations, prepare first a stock solution by stirring the sample magnetically in a suitable amount of water for about 30 minutes before preparing the final dilution by further dilution with water. The stock solution is stable for several hours at 5° C but the highly diluted final dilution should be used within 5 minutes. For the assay of unknowns it is necessary to find the suitable dilution by trial. Preparations whose activity is approximately known should be diluted to one to 3.6 lipase units/ml. The term "lipase units" is defined below.

Procedure.

Emulsion and buffer are premixed in a 3:1 weight ratio, respectively, to provide the substrate. 8.0 ml. portions of substrate are introduced into 100 ml. beakers containing magnetic stirring bars. Stir the substrate solution magnetically. Run each sample replicate (blank and sample) containing substrate as follows:

Blank

1. Add 40 ml. ethyl alcohol.
2. Add 2.0 ml. sample of enzyme solution.

Sample

1. Equilibrate substrate in a 30° C water bath.
2. Add 2.0 ml. sample of enzyme solution.
3. Incubate at 30° C for 5.0 minutes.
4. Add 40 ml. ethyl alcohol.

Titrate both blank and sample with 0.02N NaOH to pH 8.0.

Calculations.

1. Lipase Unit (LU) = quantity of lipase required by yield 1 micromote H+/minute Lipase Activity (LA) = number of LU/gram of preparation LA = ml NaOH × N NaOH × $10^3$/mg enzyme preparation added × $10^-$ × minutes When 0.02 N NaOH and a 5 minute reaction time are used, LA = ml NaOH × 4000/mg enzyme U.S.P. = United States Pharmacopocia
N.F. = National Formulary
C.P. = Chemicaly Pure It will be understood that the present invention is not limited to the foregoing methods for measuring esterase activity and lipase activity, as other methods and modifications of the foregoing methods will be apparent to the person skilled in the art after reading the disclosure herein.

Production of the desired lipolytic enzyme flavoring system can be carried out by conventional fermentation procedures followed by appropriate recovery methods. Thus, a nutrient medium containing assimilable carbon, nitrogen and trace minerals is incubated with a culture of a species of Mucor, especially *Mucor miehei*, and fermented under submerged aerobic conditions at a pH of from about 3 to 8 and a temperature of from about 20° to 50° C for about 2 to 14 days. Examples of selected strains of *Mucor miehei* which can be fermented thusly to produce the desired enzyme flavoring system are available to the public without restriction under the code designations NRRL A 13,131 and A 13,042 at the Northern Regional Research Laboratories, Peoria, Illinois. Other suitable strains of *Mucor miehei* will be readily apparent to the person skilled in the art after reading the disclosure herein.

According to prior practice, esterases and lipases generally have been either removed or inactivated as an adjust to the recovery of the desired rennet product such as described in U.S. Pat. Nos. 3,616,233 and 3,763,011, German Offen. 2,232,996, and British Pat. No. 1,207,892.

In accordance with the present invention, the desired enzyme flavoring system is recovered by separation from the fermentation mash such as to provide a suitable EA/LA ratio as herein defined. This can be carried out by filtration of the mash at acid pH of about 4–5, extraction of the filter cake at alkaline pH of about 10–12, acidification of the extract to a pH of about 7, and then recovering by filtration or concentrating the acidified extract by evaporation or ultrafiltration and then drying the concentrate such as by spray drying and the like.

It will be appreciated that for certain uses it is desirable to employ a lipolytic enzyme system that is also substantially free from rennet enzyme activity. This can be achieved by employing the foregoing recovery procedure or other purification techniques which will be apparent to the person skilled in the art.

The recovered lipolytic enzyme flavoring system can be added to milk, milk fat, butter oil, cheese, milk chocolate, margarine oil, coffee whiteners, and other triglyceride fat bearing foods and food components and incubated at temperatures ranging from about 10° to 50° C for about 2 hours to 20 days to produce desirable milk and butter like flavors. It can be used to accelerate or intensify naturally developed flavors in these foods and food components and can be blended with known flavor developing agents to produce a variety of flavor profiles. For example, it can be blended with pregastric esterase enzyme compositions of U.S. Pat. No. 2,531,329 (available as Italase from Dairyland Food Laboratory), or it can be used together with the Penicillium roqueforti-developed flavoring compositions of U.S. Pat. No. 3,100,153. Generally, the recovered lipolytic enzyme is added in amounts from about 0.001% to 0.1% by weight of the triglyceride fat-containing substrate and in the case of milk preferably in amounts from about ⅛ to 2 ounces/1000 pounds of milk.

Examples of triglyceride fats which can be treated with the lipolytic enzyme flavoring system of this invention to develop desirable flavors are animal fats such as milk fat, lard and tallow, and vegetable fats such as cottonseed oil, soybean oil, corn oil, peanut oil, safflower oil, palm oil, coconut oil and margarine and shortening oil blends.

Examples of cheeses wherein the lipolytic enzyme flavoring system of this invention can be used to develop desirable flavors are Provolone, Romano, Feta, Pizza, Mozzarella, Cheddar, Swiss, Blue, Parmesan, Colby, Gouda, and Edam.

The following examples will further illustrate the invention although it will be understood that the invention is not limited to these examples which are given by way of illustration and not limitation.

Example 1

*Mucor miehei*, NRRL 13,042, is transferred from an agar slant under aseptic conditions into a one liter Erlenmeyer flask containing 200 ml. of the following medium:

| | |
|---|---|
| Soybean Flour (Nutrisoy 300 C) | 1.5% |
| Dried Whey | 3.0 |
| Enzymatically Degraded Cornstarch | 12.0 |
| Water | 83.5 |
| Total | 100.0% |

The flask is incubated on a rotary shaker at 37° C for 114 hours starting with an initial pH of about 6. The desired lipolytic enzyme system is recovered as follows: The fermentation broth is adjusted to pH 5 and then filtered. The filtrate is extracted with dilute NaOH solution at pH 10-11 and the extract acidified to pH 7. The acidified extract is then filtered and evaporated to a concentrate having an EA value of 25.8 and an EA/LA ratio of 2.6 in one recovery run (A); and is filtered, evaporated and spray dried to a solid having an EA/LA ratio of 3.5 in another recovery run (B).

*Mucor miehei* derived lipolytic enzyme produced as above in recovery run A with the stated EA/LA ratio of 2.6 is used to develop a desirable cheese flavor as follows:

One pound samples of Current A Cheddar cheese (2-4 week old cheese, having a bland flavor) are ground with a Sunbeam table model electric grinder and the lipolytic enzyme blended therewith by further mixing until evenly distributed in proportions of 440 milligrams per pound of cheese. The blended enzyme-cheese combinations are then filled into sterile plastic petri dishes. The dishes are placed in an anaerobic container to inhibit mold growth and several samples are incubated for 4 days at 20° C and other samples are incubated for 11 days at 20° C. After the foregoing incubation periods, the cheese was tasted for its organoleptic properties and was found to have a clean flavor profile similar to that produced by commercially available pregastric Esterase C (Dairyland Foods Laboratory) tested in the identical manner. Both cheeses developed a desirable slight to medium rancidity. By way of comparison, an esterase preparation obtained from *Aspergillus flavus* was found to have an EA/LA ratio of 0.08 and in the foregoing test produced an undesirably harsh butyric-caproic-capric type profile and a slight metallic after taste.

EXAMPLE 2

*Mucor miehei*, NRRL 13,042, was used to prepare a lipolytic enzyme system as in Example 1 except that the fermentation was carried out in a production tank with an aqueous nutrient medium containing 16% corn starch liquified with bacterial α-amylase, 4% Kaysoy defatted soy bean meal and 2% spray-dried sweet whey. Upon harvest after 77 hours fermentation, the mash was assayed for EA and LA values as follows:

EA = 24.9
LA = 2.8
EA/LA = 8.9

The lipolytic enzyme product is recovered and used to develop a desirable cheese flavor as in Example 1 with substantially equivalent good results.

In the following Examples, the *Mucor meihei* lipolytic enzyme is the enzyme system prepared according to the procedure of both Examples 1 and 2, above, having EA values ranging from 10 to 100.

EXAMPLE 3

*Mucor meihei* lipolytic enzyme is added to cheese milk prior to the addition of the starter culture in an amount of ⅛-2 oz./1,000 lbs. milk for the development of controlled lipolysis to produce flavors ranging from delicate and buttery to peppery and sharp "piccante" in the manufacture of Italian-type varieties of cheese, namely Asiago-Mozzarella, Provolone and Romano, respectively, with cheese milk for Romano and other sharp flavored varieties receiving the higher levels of lipolytic enzyme treatment.

EXAMPLE 4

*Mucor miehei* lipolytic enzyme is added to cheese milk prior to addition of the starter culture in an amount of ⅛-¼ oz./1,000 lbs. milk for the development of controlled lipolysis to produce greater amounts of short chain fatty acids relative to long chain fatty acids to be metabolized with the end products of Penicillium roqueforti spores to produce a desirable flavor and level of methyl ketones and $CO_2$ in Blue Cheese and Blue Cheese flavor.

EXAMPLE 5

*Mucor miehei* lypolytic enzyme is added to the macerated form of Cheddar, Colby, Romano, Swiss, Mozzarella, Blue, Gouda, Edam, Provolone, and Parmesan in the percentage of 0.01% to 0.1% of the ground cheese weight or cheese solids both with and without other enzymes to produce enzyme modified cheeses of high flavor for use in replacement of cheese solids in the manufacture of pasteurized process cheese, cheese food, cheese spread, cheese powder, cheese snacks, cheese sauces, cheese dips and salad dressings. To obtain flavor stability, the lipolytic enzyme is inactivated in the enzyme modified cheese by treatment of the product at 70° C for 15 minutes at pH 5.0.

EXAMPLE 6

Butter prepared from churned cream and washed with water is converted to butteroil by warming to 39° C and centrifuging to remove the residual butter serum. Butteroil of this general type is treated with *Mucor miehei* lipolytic enzyme in the percentage of 0.005% to 0.05% of the butterfat weight of the sterilized butteroil. The lipolytic enzyme treated butteroil is incubated at 22° C to 37° C for 1-3 days for proper flavor development prior to inactivation at 70° C for 15 minutes at pH 5.0. Lipolytic enzyme-treated butteroil is used both alone and with other flavor acids, namely acetic and butyric, and/or other flavor chemicals, namely diacetyl, as a flavoring agent and texturizing agent in butter flavor, margarine, imitation milk products, candies of a milk chocolate type, and butter spreads and sauces.

EXAMPLE 7

*Mucor miehei* lipolytic enzyme is added to 200 times its weight of sterilized cream having 35% butterfat content. After the cream is adjusted to an acid pH with lactic acid or lactic culture, the mixture is stirred at 37° C for 4 hours. The resulting mixture is subjected to a conventional method for the preparation of butter to yield butter having an excellent, improved flavor.

EXAMPLE 8

*Mucor miehei* lipolytic enzyme is added in the percentage of 0.001% to 0.01% both with and without other enzyme systems to a reconstituted slurry of 9-14% whole fat milk solids prior to 22° C – 33° C incubation for 4-8 hours. The controlled lipolysis is inactivated in a manner similar to that described in Example 6. This lipolytic enzyme modified whole milk powder is used to impart dairy type flavor to food products such as milk chocolate candies, coffee whiteners, imitation cheese and dairy food products.

EXAMPLE 9

*Mucor miehei* lipolytic enzyme modified cheese solids prepared as in Example 5 is used in pet food formulations, namely dog food formulations in the percentage of 1.0% to 10.0% of the total solids of the formulation, to impart a nutritious, improved flavor to the pet food formulation.

EXAMPLE 10

*Mucor miehei* lipolytic enzyme is used to treat salvage cheese by procedure as described in Example 5 followed by heat treatment at 77° C for 15 seconds to destroy the undesirable mold and bacteria in the salvage cheese and to effectively inactivate the lipolytic enzyme in the product. The lipolytic enzyme-treated salvage cheese is acceptable for pet food formulations.

EXAMPLE 11

*Mucor miehei* lipolytic enzyme-treated (modified) whole milk powder prepared as in Example 8 is used in the percentage of 5.0% to 15.0% in the manufacture of an improved, fuller flavored coffee whitener.

EXAMPLE 12

*Mucor miehei* lipolytic enzyme-treated (modified) whole milk powder prepared as in Example 8 is used in the percentage of 2.0% to 10.0% in the manufacture of an improved, richer, fuller flavored imitation sour cream.

EXAMPLE 13

A Bleu cheese is made from raw milk, homogenized at 90° F and bleached with benzoyl peroxide. The milk is heated to 86° F and inoculated with one percent of a *Streptococcus lactis* starter. After a brief holding period, the milk is inoculated with a microbial rennin product from the growth of the strain of *Mucor miehei* designated NRRL A 13,042 in an amount of 3 ounces per 1000 pounds of milk, and -¼ ounces of *Mucor miehei* lipolytic enzyme per 1000 pounds of milk. The mixture is agitated until a curd of satisfactory firmness is obtained. The curd is then inoculated with spores of *Penicillium roqueforti*, separated from the whey and transferred to hoops. The hooped curd is salted by immersing in brine for 3 days and packaged in an evacuated plastic ("Cryovac") bag. Pin holes are made throughout the cheese to admit air and facilitate growth of the mold. The cheese is then ripened by placing in a curing room for two months at 50° F and 90% humidity to produce an excellent quality Bleu cheese with an improved flavor over that obtained without the added lipolytic enzyme.

EXAMPLE 14

A Romano type cheese is made from partially skimmed milk containing about 2% fat. The milk is warmed to 88° - 90° F and one percent of equal proportions of *Streptococcus thermophilus* and *Lactobacillus bulgaricus* cultures is added. Rennet is added in sufficient quantity to coagulate the milk in 15 - 17 minutes (about 3 ounces per 1000 pounds). *Mucor miehei* lipolytic enzyme is added at the rate of 1 to 2 ounces per 1000 pounds of milk. The resulting curd is cut with ⅜ inch knives. After cutting, the curd is cooked at 116° - 118° F for 30 minutes and then separated from the whey. The curd is placed in hoops, pressed, shelf dried for 2 - 4 days and then salted to a salt content of 4 - 5%. The cheese is then cured at 50° -60° F and relative humidity of 70% to produce an excellent quality Romano cheese of improved flavor over that obtained without the added lipolytic enzyme.

EXAMPLE 15

A liquid shortening as disclosed in U.S. Pat. No. 2,815,286 and a plastic shortening as disclosed in U.S. Pat. No. 2,132,393 are each incubated with 1% to 15% by weight of *Mucor miehei* lipolytic enzyme at 90° F for one to 24 hours to develop desirable flavors followed by inactivation of the enzyme at 70° F for 15 minutes at pH 5.0.

Various other examples and modifications of the foregoing examples will be apparent to the person skilled in the art after reading the foregoing specification without departing from the spirit and scope of the invention. All such further examples and modifications are included within the scope of the appended claims.

What is claimed is:

1. A method for producing a lipolytic enzyme system having esterase and lipase activity in a ratio of from 1 part of lipase activity to from 1 to about 10 parts of said esterase activity, said method comprising culturing *Mucor miehei* on a nutrient medium and recovering said lipolytic enzyme system substantially free of *Mucor miehei* rennet activity.

2. The method of claim 1 wherein the system is recovered substantially free of rennet activity by acidifying the cultured medium and recovering the lipolytic enzyme system - containing filter cake.

3. The method of claim 1 wherein the *Mucor miehei* is selected from the group consisting of NRRL A 13,131 and NRRL A 13,042.

4. The method of claim 1 wherein the ratio is from about 1 of lipase activity to between about 2 to about 10 parts of esterase activity.

5. A *mucor miehei* enzyme system obtained by the method of claim 1 having esterase and lipase activity in a ratio of from 1 part of said lipase activity to between 1 and about 10 parts of said esterase activity.

6. A method of producing a lipolyzed triglyceride fat-containing food component selected from the group consisting of vegetable fat, butteroil and tallow which comprises contacting said component with a lipolyzing amount of the claim 5 enzyme system.

7. A method for producing a lipolyzed whole milk powder of enhanced flavor which comprises contacting said powder with a lipolyzing amount of the claim 5 enzyme system.

8. A method for producing a lipolyzed triglyceride fat-containing food component consisting essentially of milk fat, which comprises contacting said component with a lipolyzing amount of the claim 5 enzyme system.

9. The method of claim 6 in which the component comprises a vegetable fat.

10. In the method for producing lipolyzed triglyceride fat-containing foods of enhanced flavor which comprises developing the flavor of said food by contacting said food with a lypolyzing amount of an animal-derived lipolytic enzyme agent, the improvement comprising using in place of at least a portion of said enzyme agent a lipolytic enzyme system having esterase and lipase activity in a ratio of from one part of said lipase activity to between 1 to about 10 parts of said esterase activity, said system obtained by culturing *Mucor miehei* on a nutrient medium and recovering said system substantially free of *Mucor miehei* rennet activity.

11. The method of claim 10 wherein the animal-derived enzyme agent is pregastric esterase.

12. The method of claim 10 wherein the food is cheese.

13. The method of claim 12 wherein the cheese is an Italian variety of cheese.

14. The method of claim 10 wherein the enzyme system is used in place of all of the enzyme agent.

15. A method for producing a lipolytic enzyme system having both esterase activity and lipase activity in a ratio of about from 2 to 10 parts of esterase activity to one part of lipase activity, said method comprising (a) culturing *Mucor miehei* on a nutrient medium to produce a mash; (b) filtering the mash at a acid pH, thus producing a filter cake; (c) extracting the filter cake at alkaline pH; and (d) acidifying the extract to a pH of about 7, thus obtaining a lipolytic enzyme substantially free of rennin and having both esterase activity and lipase activity in a ratio of about from 1 to 10 parts of esterase activity to one part of lipase activity.

16. A method for producing enzyme modified butteroil of enhanced flavor, said method comprising contacting butteroil with a lipolyzing amount of the claim 15 lipolytic enzyme system and incubating to effect lipolysis.

17. The method of claim 16 wherein the system is inactivated after incubation.

18. A method for producing enzyme modified whole milk powder, said method comprising contacting whole milk powder with a lipolyzing amount of the claim 15 lipolytic enzyme system and incubating to effect lipolysis.

19. The method of claim 18 wherein the system is inactivated after incubation.

20. A *Mucor miehei* enzyme system obtained by the method of claim 15 having esterase and lipase activity in a ratio of from 1 part of said lipase activity to between 1 and about 10 parts of esterase activity.

21. A method for producing enzyme modified tallow, comprising contacting tallow with a lipolyzing amount of the claim 15 lipolytic enzyme system and incubating to effect lipolysis.

* * * * *

UNITED STATES PATENT OFFICE
CERTIFICATE OF CORRECTION

Patent No. 4,065,580      Dated Dec. 27, 1977

Inventor(s) LOUIS I. FELDMAN and GORDON DOOLEY

It is certified that error appears in the above-identified patent and that said Letters Patent are hereby corrected as shown below:

| Col. | Line | | |
|------|------|---|---|
| 3 | 35 | | "subtrating" should be --substracting-- |
| 4 | 35 | | "neddle" should be --needle-- |
| 4 | 36 | | "1- inches)" should be --1-1/2 inches)-- |
| 4 | 61 | | "HCI" should be --HCl-- |
| 5 | 35 | | "10-" should be --$10^{-3}$-- |
| 5 | 31 | | "H+/minute" should be --$H^+$/minute-- |
| 5 | 67 | | "adjust" should be --adjunct-- |
| 6 | 33&34 | | "Penicillium roqueforti" should be italicized. |
| 8 | 8&9 | | Same as above |
| 9 | 36 | | "-1/4" should be --1/8-1/4-- |
| 9 | 60 | | "3/4" should be --3/8-- |
| 10 | 23 | Claim 1 | "rennet" should be written as normally |

Signed and Sealed this

*Twenty-fifth* Day of *April 1978*

[SEAL]

*Attest:*

RUTH C. MASON
*Attesting Officer*

LUTRELLE F. PARKER
*Acting Commissioner of Patents and Trademarks*